United States Patent [19]

Itoh

[11] Patent Number: 5,013,529
[45] Date of Patent: May 7, 1991

[54] APPARATUS FOR DISTRIBUTING SAMPLE LIQUID

[76] Inventor: Teruaki Itoh, 5-25, Kokaihonmachi, Kumamoto-shi, Kumamoto-ken, Japan

[21] Appl. No.: 474,257

[22] Filed: Feb. 6, 1990

Related U.S. Application Data

[63] Continuation of Ser. No. 187,737, Apr. 29, 1988, abandoned.

[30] Foreign Application Priority Data

| May 2, 1987 | [JP] | Japan | 62-67021 |
| May 2, 1987 | [JP] | Japan | 62-67022 |
| May 2, 1987 | [JP] | Japan | 62-67023 |
| May 2, 1987 | [JP] | Japan | 62-67024 |

[51] Int. Cl.$^5$ .......................................... G01N 35/00
[52] U.S. Cl. ..................................... 422/100; 422/63; 422/65; 73/863.01; 73/864.11
[58] Field of Search ............ 422/65, 81, 100, 63; 141/94, 95; 73/863.01, 863.02, 864.11, 864.15, 864.16; 222/64

[56] References Cited

U.S. PATENT DOCUMENTS

| 3,893,493 | 7/1975 | Foirest et al. ................ 141/47 |
| 3,894,438 | 7/1975 | Ginsberg .................... 73/863.01 |
| 4,076,503 | 2/1978 | Atwood et al. ............... 422/100 |
| 4,586,546 | 5/1986 | Mezei et al. |
| 4,692,308 | 9/1987 | Riley et al. .................. 422/65 |
| 4,727,033 | 2/1988 | Hijikata et al. .............. 436/69 |
| 4,777,832 | 10/1988 | Prodosmo et al. ............ 73/863.02 |
| 4,780,833 | 10/1988 | Atake ........................... 73/864.14 |
| 4,794,085 | 12/1988 | Jessop et al. ................ 436/54 |
| 4,810,659 | 3/1989 | Higo et al. .................... 422/82 |
| 4,830,832 | 5/1989 | Arpagaus et al. ............. 422/100 |

FOREIGN PATENT DOCUMENTS

| 169071 | 1/1986 | European Pat. Off. |
| 210014 | 1/1987 | European Pat. Off. |
| 273128 | 7/1988 | European Pat. Off. |
| 126473 | 6/1986 | Japan |
| 250561 | 11/1986 | Japan |
| 15121 | 1/1988 | Japan |

OTHER PUBLICATIONS

Patent Abstracts of Japan, vol. 6, No. 51, (P-108) [929], Apr. 6, 1982, JP-56-164,958 (Aroka K.K.).
Patent Abstracts of Japan, vol. 8, No. 157, (P-288) [1594], Jul. 20, 1984, JP-59-52,759 (Terumo K.K.).
Patent Abstracts of Japan, vol. 10, No. 330, (P-514) [2386], Nov. 11, 1986, JP-61-137,067 (Toshiba Corp.).

*Primary Examiner*—Robert J. Warden
*Assistant Examiner*—D. John Griffith, Jr.
*Attorney, Agent, or Firm*—Nixon & Vanderhye

[57] ABSTRACT

An apparatus for distributing sample liquids from source test tubes into destination test tubes. It has distribution tips and air-supply devices for supplying air to the tips at a low rate. The tips are lowered into the source tubes, while air is flowing from the devices and through the tips. The moment the tips reach the surface levels of the liquids contained in the source tubes, the air pressure changes. When this change is detected, the tips start sucking the liquids from the source tubes. An apparatus similar to the above-mentioned one. It has distribution units each having a tip, a lever having a slit, and pins projecting from the units and inserted in the slit. The lever is rotated, changing the interval between the distribution units to the interval between the source or the destination tubes held in a rack. A similar apparatus which has distribution tips and a tray. The tray is kept away from below the tips while the sample liquids are being sucked into the tips from the source tubes or being distributed from the tips into the destination tubes, and is placed below the tips while the tips are being moved. A similar apparatus which has distribution units each having a tip, and a jig having cut-outs. The jig holds tips in the cut-outs as the distribution units are moved upward from the jig, whereby the tip are detached from the units.

3 Claims, 5 Drawing Sheets

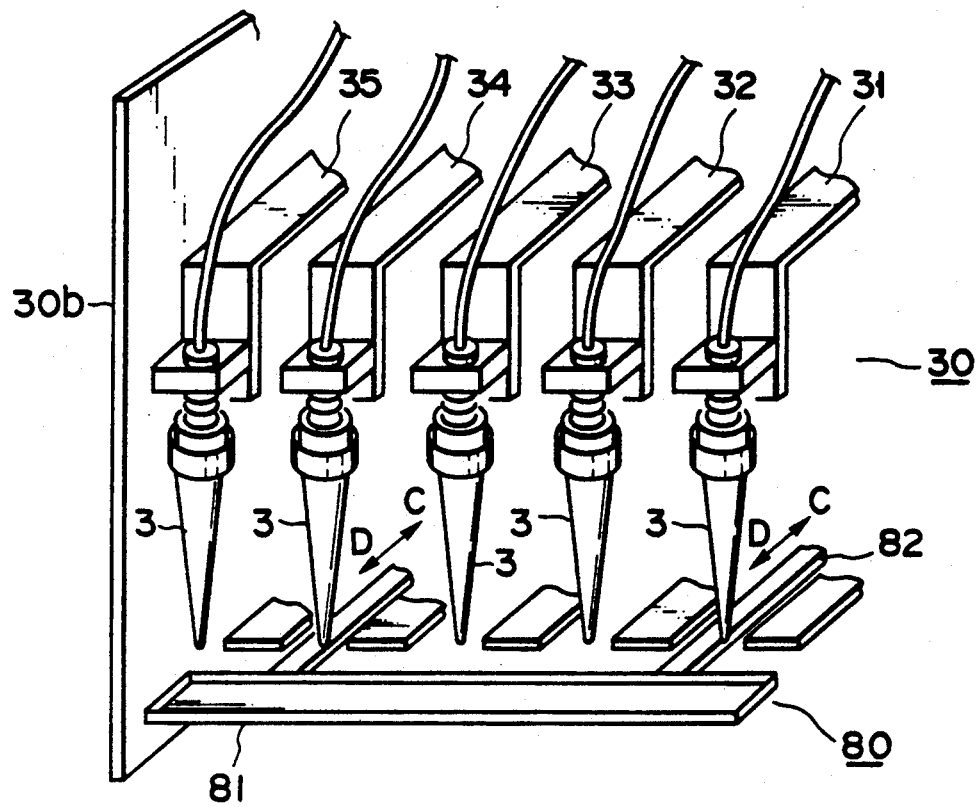
F I G. 5
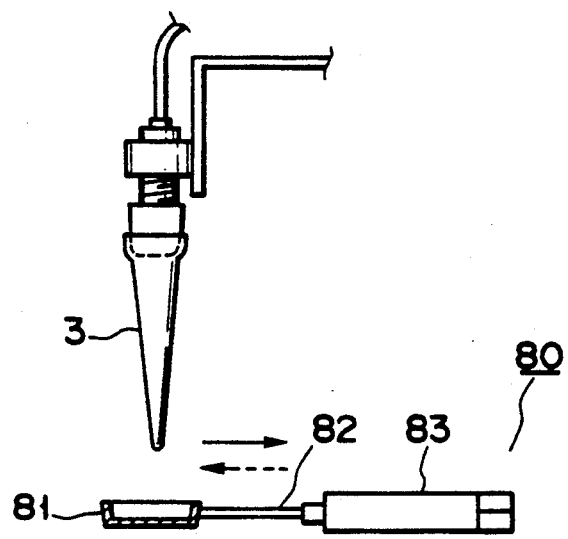
F I G. 6

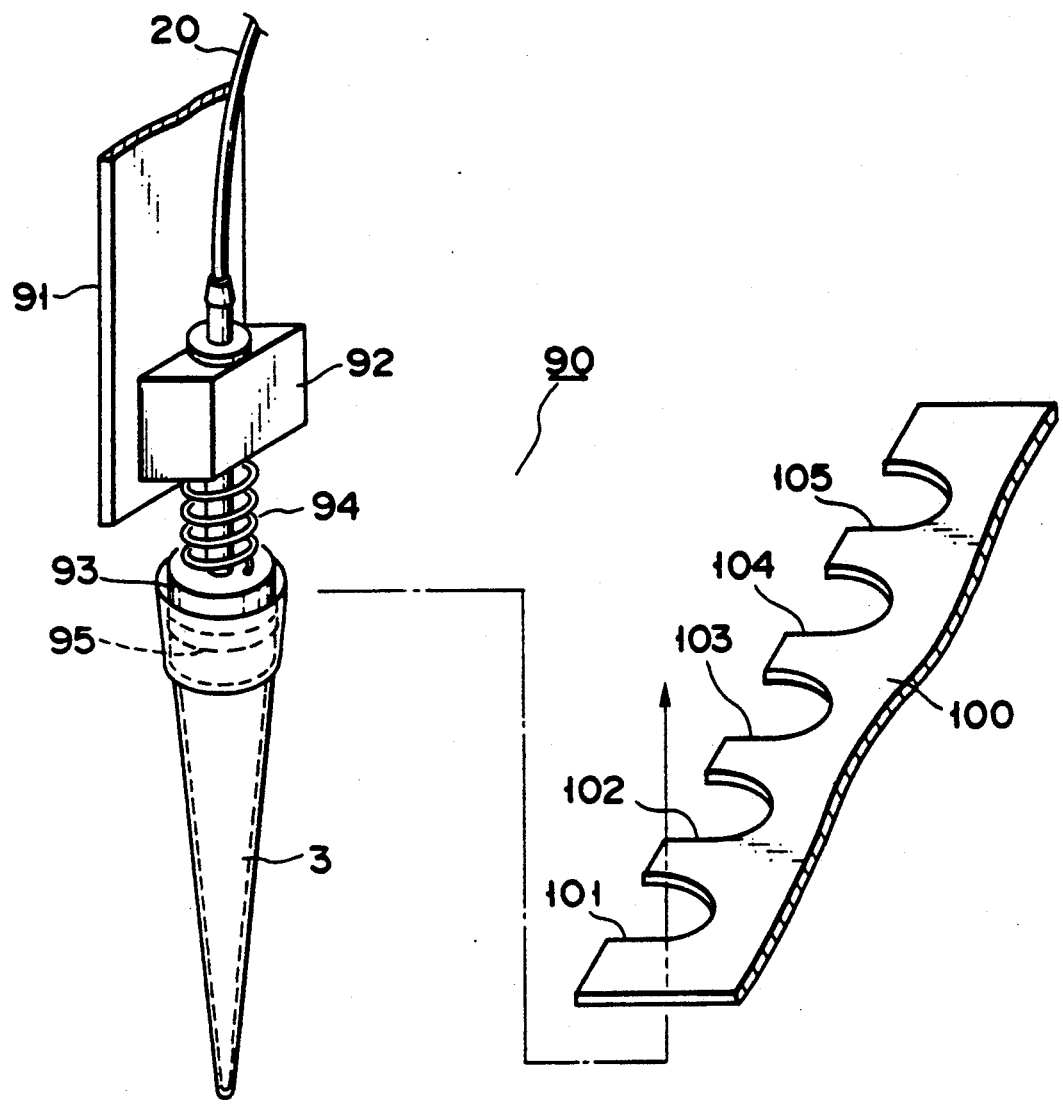
F I G. 7

APPARATUS FOR DISTRIBUTING SAMPLE LIQUID

This is a continuation of application Ser. No. 07/187,737, filed Apr. 29, 1988, now abandoned.

BACKGROUND OF THE INVENTION

1. Field of the Invention

The present invention relates to an apparatus for distributing sample liquid, such as sampled blood, from a test tube into a plurality of other tubes, so that the distributed portions of the sample liquid are subjected to different items of analysis.

2. Description of the Related Art

In order to analyze sample liquid, such as blood, thereby to determine whether or not germs are contained in the liquid, and what kinds of germs they are, if contained in the liquid, it is necessary to distribute the sample liquid into a plurality of test tubes, to sort the test tubes containing the distributed portions of the liquid into groups in accordance with items of analysis, and to supply these test tubes, thus sorted, to various analyzers for performing the items of analysis on the sample liquid. Analyzers have been developed, and greatly improved analyzers have been put to practical use. The blood analyzer is a good example. Nonetheless, the distribution of a liquid sample is performed solely by human labor, as is seen in the hospitals and the research institutes. No automatic apparatus for distributing a sample liquid into a plurality of test tubes or the like have been developed.

There are problems with the distribution of a sample liquid carried out by human labor. First, the sample liquid may spill, wetting the hands of the persons engaged in the distribution of the liquid, or staining the floor. Secondly, the test tube from which the sample liquid is being distributed, or the test tubes into which the liquid is being distributed may be dropped, by mistake, onto the floor, inevitably staining the floor. Thirdly, the sample-distribution by means of manual labor requires a long time and is error-prone. Because of these problems, it is difficult to keep the sample-distribution room sufficiently clean and sanitary, or to accomplish a sufficiently high work efficiency.

The inventors hereof studied the possibility of developing an apparatus which has distribution tips, vacuum means for supplying a sample liquid into the tips from a test tube, transport means for moving the tips containing the liquid to other test tubes, and sample-distributing means for distributing the portions of the sample liquid from the tips into the test tubes. They found that such an apparatus cannot be practically employed unless it satisfies the following requirements:

(1) Each distribution tip must be set in a test tube at such an appropriate level that the sample liquid can be supplied into the tip from the test tube, without using a complex sensor (e.g., a photosensor) for detecting the surface level of the liquid in the tube or a complex control device for moving the tip to the desired level in accordance with the signal output by the sensor and representing the surface level of the liquid.

(2) The distribution tips must be arranged quickly and precisely at the same intervals as the test tubes which are held in a rack and into which the sample liquid will be distributed. This is because various kinds of racks are used, each having holes for holding test tubes at regular intervals specific to the rack.

(3) Measures must be taken to prevent the sample liquid from dribbling into the test tubes other than the desired ones while the distribution tips are being moved from the source tubes to the destination tubes, due to the vibration or the like applied to the distribution tips during the transportation.

(4) Means must be used to replace the distribution tips with new and clean ones, smoothly and quickly, every time a sample liquid has been distributed from the tips into test tubes.

SUMMARY OF THE INVENTION

It is accordingly the first object of the present invention to provide an apparatus which can automatically distribute a sample liquid from distribution tips into test tubes, without dropping the liquid onto the floor, and which can set each distribution tip in the test tube at an appropriate level, without using a complex sensor, such as a photosensor, thereby accomplishing a sufficiently efficient sample-distribution.

The second object of the invention is to provide an apparatus which can automatically distribute a sample liquid from distribution tips into test tubes, and can quickly arrange the distribution tips at the same intervals as the test tubes.

The third object of this invention is to provide an apparatus which can automatically distribute a sample liquid from distribution tips into test tubes, and can prevent the sample liquid from dribbling from the tips into test tubes other than the destination ones while the tips are being moved from the source tubes to the destination tubes, due to the vibration or the like applied to the tips during the transportation.

The fourth object of the present invention is to provide an apparatus which can automatically distribute a sample liquid from distribution tips into test tubes, and can automatically replace the distribution tips with new and clean ones, quickly and smoothly.

To achieve the first object of the invention, there is provided an apparatus comprising distribution tips, vacuum means for supplying a sample liquid from a source test tube into the distribution tips, transport means for moving the tips containing the sample liquid to destination tubes, and sample-distributing means for distributing the portions of the sample liquid from the tips into the destination tubes. The distribution tips are connected to air pipes. The air pipes are connected to changeover valves, respectively. Each changeover valve has two air-inlet ports. The first air-inlet port is connected to a pressure detector, which in turn is coupled to an air supply device. The second air-inlet port is connected to an air cylinder containing a piston. The pressure detector generates an electric signal upon detecting a change in the pressure of the air being supplied from the air supply device, and supplies this signal to the changeover valve. In response to the signal, the valve connects the air pipe to the air supply device or the piston/cylinder device. When the pipe is connected to the air supply device, the sample liquid can be sucked from the source tube into distribution tip by moving the piston in a first direction, or supplied from the tip into the destination tube by moving the piston in a second direction opposite to the first direction.

In operation, the air supply device is started, air is supplied from the distribution tip at a low rate. The tip is gradually lowered into the source tube. When the tip reaches the surface of the sample liquid contained in the tube, the air pressure of the air being supplied from the air supply device changes, whereby the pressure detector generates a signal. In response to this signal, the changeover valve connects the air pipe to the air cylinder. The piston of the air cylinder is moved in the first direction, whereby a portion of the liquid is sucked up into the distributing tip and retained therein. Then, the distribution tip is moved from the source tube to the destination tube. The piston is moved in the second direction, whereby the liquid is distributed from the tip into the destination tube. Thus, no sensors are required to detect surface level of the liquid in the source tube to set the tip at an appropriate position within the source tube.

To attain the second object of the invention, there is provided an apparatus which comprises distribution tips, vacuum means for supplying a sample liquid from a source test tube into the distribution tips, transport means for moving the tips containing the sample liquid to destination tubes, and sample-distributing means for distributing the portions of the sample liquid from the tips into the destination tubes. The apparatus further comprises a sample-distributing section having distribution units. Each of the distribution units has a tip holder for holding the distribution tip. Pins protrude from the tip holders holding the distribution tips, or from the members supporting the tip holders. The tip holders are therefore, set apart at regular intervals, and the pins are, also, set apart at regular intervals. These pins are inserted in the slit cut in a slanting lever. The lever is fixed at one end and can be rotated by drive means such as a pulse motor.

In operation, when the lever is rotated in either direction by the drive means, the intervals between the pins are changed. Hence, the regular intervals among the distribution tips are also changed. In this way, the distribution tips can be set at the same regular intervals as the destination test tubes, whereby portions of the sample liquid are simultaneously distributed into these test tubes.

To achieve the third object of the invention, there is provided an apparatus which comprises distribution tips, vacuum means for supplying a sample liquid from a source test tube into the distribution tips, transport means for moving the tips containing the sample liquid to destination tubes, and sample-distributing means for distributing the portions of the sample liquid from the tips into the destination tubes. The apparatus further comprises a sample-distributing section having distribution units and a plurality of cups. Each distribution unit has a tip holder for holding the distribution tip. The cups are positioned below distribution tips held by the holders, while the tips are being moved from the source tubes to the destination tubes, and vice versa, and are moved by drive means and remain away from the tips while the sample liquid is being sucked up into, or supplied from, the distribution tips. Thus, the liquid, if dribbling from the tips during the transport of the tips, falls into the cups, not into test tubes other than the destination tubes.

To accomplish the fourth object of the invention, there is provided an apparatus which comprises distribution tips, vacuum means for supplying a sample liquid from a source test tube into the distribution tips, transport means for moving the tips containing the liquid to destination tubes, and sample-distributing means for distributing the portions of the sample liquid from the tips into the destination tubes. The apparatus further comprises a jig and a sample-distributing section having distribution units. Each distribution unit has a tip holder and a plug attached to the holder. The plug has an O-ring mounted on it, and can be removably fitted in the proximal end of the distribution tip held by the holder. The jig is a rectangular plate having a semicircular notches cut in one side. The notches have a radius such that the plugs can be inserted into them, but the proximal ends of the tips cannot be inserted into them. The jig can be moved relative to the distribution tips, in both the vertical direction and the horizontal direction. In operation, when the jig or the tips are moved vertically and horizontally, the distribution tips are easily attached to, for detached from, the distribution units.

BRIEF DESCRIPTION OF THE DRAWINGS

FIG. 5 is a perspective view of the distributing section, as is viewed from the front;

FIG. 6 is a side view of one of the distribution units included in the sample-distributing section; and FIG. 7 is a perspective view of the mechanism used in the apparatus, for attaching distributing tips to, and detaching them from, the sample-distributing unit.

DETAILED DESCRIPTION OF THE PREFERRED EMBODIMENTS

Figures 1, 2:
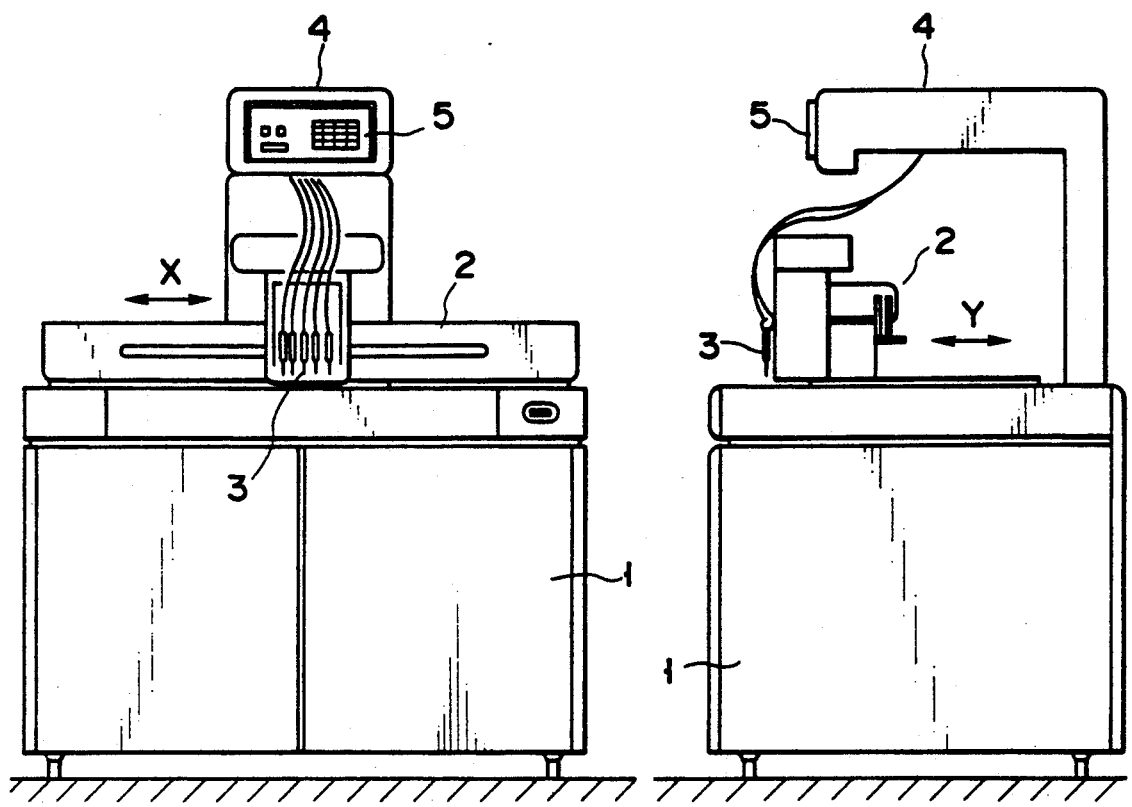
FIG. 1 is a front view of an apparatus according to the present invention.
FIG. 2 is a side view of the apparatus illustrated in FIG. 1.

FIGS. 1 and 2 show an apparatus according to the present invention, which can automatically distribute a sample liquid from a source test tube into a plurality of destination test tubes. As is illustrated in these figures, the apparatus comprises housing 1, movable bed 2 mounted on housing 1, a sample-distributing section attached to bed 2 and including five distribution tips 3, L-shaped post 4 having a vertical portion protruding upward from housing 1 and a horizontal portion extending from the vertical portion, and console panel 5 attached to the free end of L-shaped post 4. Housing 1 contains a control system including a sequencer. Bed 2 can be moved in the direction of arrow X and also in the direction of arrow Y, as is illustrated in FIGS. 1 and 2.

Figure 3:
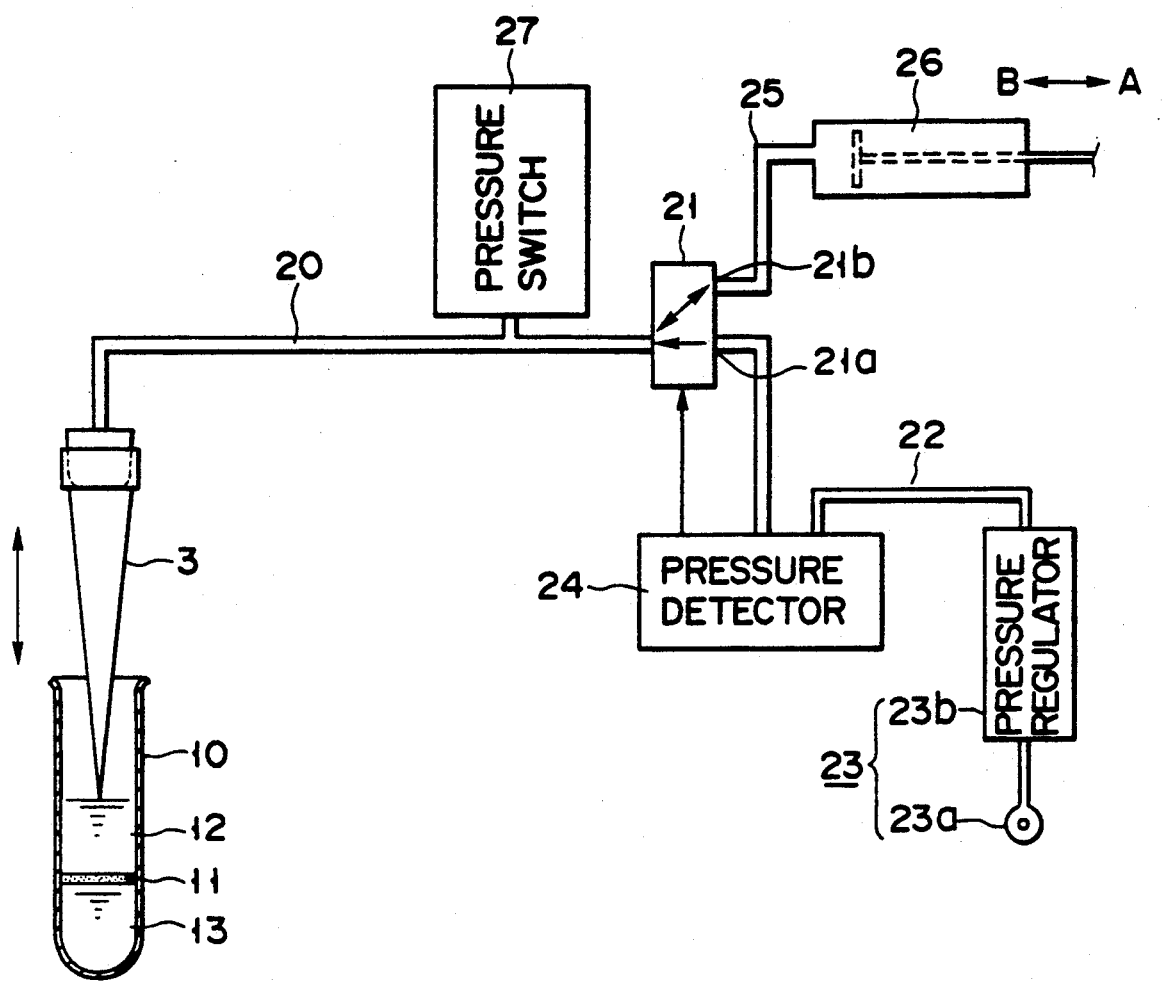
FIG. 3 is a schematic representation of the sample-distributing section incorporated in the apparatus shown in FIGS. 1 and 2.

The apparatus further comprises a sample-distribution section having five identical distribution units. FIG. 3 schematically shows the sample-distributing section. A blood sample is contained in source test tube 10, with serum 12 separated from cells 13 by separation agent 11. Each distribution tip 3 can be moved up and down by a drive mechanism (not shown), so that its distal end can be inserted into source tube 10. The proximal end of tip 3 is coupled to one end of air pipe 20 in airtight fashion. The other end of pipe 20 is connected to changeover valve 21 having two air-inlet ports 21a and 21b. First port 21a is connected by pipe 22 to air supply device 23 comprising compressed air source 23a and pressure regulator 23b. Second port 21b is connected by pipe 25 to piston/cylinder device 26. Pressure detector 24 is coupled to pipe 22, for detecting changes in the pressure of the air flowing through pipe 22. Upon detecting a change in the air pressure, detector 24 generates and supplies a signal to changeover valve 21. In response to this signal, valve 21 connects pipe 20 to pipe 25. As long as valve 21 connects pipes 20 and 25, serum 10 can be sucked from tube 10 into tip 3 and remain therein when the piston is moved in the direction of arrow A, and can be distributed from tip 10 into a destination test tube (not shown) when the piston is moved in the direction of arrow B. Pressure switch 27 is connected to pipe 20, for checking tip 3 for an abnormal condition, such as clogging.

The operation of the sample-distributing section will now be explained. First, air supply device 23 is turned on, whereby air is supplied at a low rate to tip 3 through pressure detector 24, and changeover valve 21. Hence, the air is continuously supplied from distribution tip 3 through the distal end thereof. In this condition, tip 3 is gradually lowered into source tube 10. The moment the distal end of tip 3 reaches serum 12, the air stream meets resistance, and the pressure of air flowing through pipes 20 and 22 rises. Pressure detector 24 detects this pressure rise, and generates and supplies a signal to changeover valve 21. In response to this signal, valve 21 disconnects pipe 20 from first port 21a and connects pipe 20 to second port 21b, thus connecting pipe 20 to pipe 25. Then, the piston of piston/cylinder device 26 is moved in the direction of arrow A. As a result, serum 12 is sucked into distribution tip 3. Simultaneously, pressure switch 27 determines whether tip 3 is clogged or not. When a predetermined amount of serum 12 has been introduced into tip 3, the piston is stopped, and this amount of serum is retained in tip 3.

The amount of serum 12 contained in source tube 10 has been calculated based on the surface level of separation agent 11, the surface level of serum 12, and the inner diameter of tube 10. Distribution tip 3 is lowered in accordance with the calculated amount of serum 12, so as to prevent its distal end from reaching separation agent 11.

Thereafter, movable bed 2 is moved toward the place where destination test tubes are located, until distribution tips 3 are positioned immediately above the destination tubes, respectively. Then, each tip 3 is lowered until its distal end enters the destination tube. The piston of piston/cylinder device 26 is moved in the direction of arrow B, whereby serum 12 is supplied from tip 3 into the destination tube. Thus, serum 12 is distributed from source tube 10 into the destination tube. Thereafter, tip 3 is replaced with a new one, so that another sample liquid is distributed from a source test tube into a destination test tube. The serum can be distributed from tip 3 into a plurality of test tubes.

Figure 4:
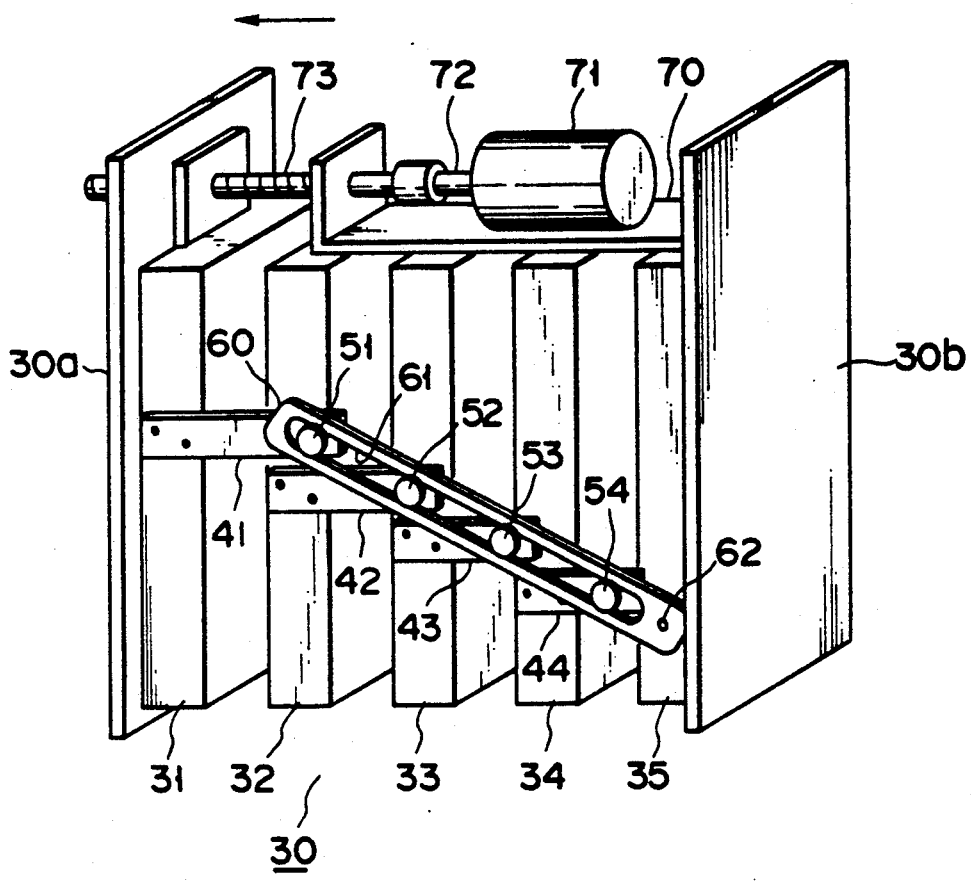
FIG. 4 is a perspective view of the sample-distributing section of the apparatus, as is viewed from the back.

FIG. 4 is a perspective view of the sample distributing section, as is viewed from the back. As is shown in this figure, the section comprises two vertical plates 30a and 30b located in a face-to-face relation, and five distribution units 31 to 35 interposed between plates 30a and 30b. Of these units, units 31 and 35 are fastened to plates 30a and 30b, respectively. The remaining units 32, 33, and 34 can slide on guide rails (not shown) which extend between plates 30a and 30b. Distribution units 31 to 35 each have a distribution tip 3 (not shown). Unit 31 is fastened to plate 30a, and unit 35 is secured to plate 30b. Rectangular plates 41 to 44 are fastened to the backs of units 31 to 34, respectively. These plates 41 to 44 extend horizontally and parallel to one another, and are staggered in the vertical direction. They have pins 51 to 55 protruding from their free ends. Pins 51 to 54 are arranged in a line inclined to the direction in which units 32, 34, and 34 can slide on the rails. Pins 51 to 54 are inserted in slit 61 cut in lever 60. Lever 60 is supported, at one end, by pivot 62 protruding from the back of distribution unit 35, and can thus rotate around pivot 62.

As is shown in FIG. 4, the sample-distributing section further comprises motor support 70 extending horizontally from the upper end of plate 30b toward plate 30a and having a rectangular portion projecting upward from the free end. Pulse motor 71 is fixed on support 70. Shaft 72 of pulse motor 71 is fastened to threaded rod 73 is fastened to shaft 72 of pulse motor 71. Rod 72 extends through the hole cut in the rectangular portion of support 70 and set in screw engagement with the screw hole cut in the upper end portion of plate 30a. Hence, When pulse motor 71 is driven in one direction, plate 30a and, thus, distribution unit 31 are moved away from plate 30b, whereby lever 60 rotates counterclockwise (FIG. 4), moving units 42, 43, and 44 such that the interval among units 41 to 45 increases. Conversely, when motor 71 is driven in the other direction, plate 30a and, thus, unit 31 are moved toward plate 30b, whereby lever 60 rotates clockwise (FIG. 4), thereby moving units 42, 43, and 44 such that the interval among units 41 to 45 decreases.

When the interval between tips 3 attached to units 31 to 35 is shorter than the interval at which test tubes are arranged from which sample liquids must be sucked up into tips 3, or into which they must be distributed from tips 3, it must be increased match to the interval of the tubes. To increase the interval between tips 3, pulse motor 71 is driven in the forward direction. Threaded rod 73 is rotated, thus moving plate 30a and distribution unit 31 in the direction of the arrow shown in FIG. 4. As a result, lever 60 rotates counterclockwise around pivot 62, thus moving distribution units 32, 33, and 34 such that the interval between units 31 to 35 increases to the interval of the test tubes.

When the interval between tips 3 is longer than the interval at which the test tubes are arranged, it must be decreased to match the interval of the tubes. To decrease the interval between tips 3, pulse motor 71 is driven in the reverse direction. Threaded rod 73 is rotated, thus moving plate 30a and distribution unit 31 in the direction opposite to the direction represented by the arrow. Here, lever 60 rotates clockwise around pivot 62, thus moving distribution units 32, 33, and 34 such that the interval between units 31 to 35 decreases to the interval of the test tubes.

Therefore, the sample-distributing section 30 can be used to distribute from source test tubes held in the holes of a rack, which are arranged at any intervals, into destination test tubes held in the holes of a rack, which are arranged at the same or different intervals.

FIG. 5 is a perspective view of distributing section 30, as viewed from the front. FIG. 6 is a side view of one of the distribution units included in the section 30. As is evident from FIGS. 5 and 6, each of distribution units 31 to 35 has distribution tip 3. Section 30 is attached to movable bed 2, and can move in the directions of arrows X and Y (FIGS. 1 and 2), along with movable bed 2. Sample-distributing section 30 has tray mechanism 80 comprising tray 81, two paralleled rods 82, and drive cylinder 83. Rods 82 connect tray 81 to drive cylinder 83.

When tips 3 are placed above source tubes to suck up serum 12 therefrom or above the destination tubes to distribute the serum thereinto, drive cylinder 83 pulls rods 82 in the direction of arrow C (FIG. 5), thus moving tray 81 from the position below tips 3. Tray 81 is no longer located between tips 3 and the source or destination tubes, and serum 12 can be sucked from the source tubes into tips 3, or distributed from tips 3 into the destination tubes. After serum 12 has been sucked into tips 3, or distributed into the destination tubes, drive cylinder 83 pushes rods 82 in the direction of arrow D (FIG. 5), thus moving tray 81 to the position below tips 3. Thus, tray 81 remains below tips 5 while tips 3 are being moved from the source tubes to the destination tubes, or vice versa. If the serum dribbles from tips 3, it falls onto tray 81, not into test tubes other than the destination tubes.

FIG. 7 is a perspective view of mechanism 90 for attaching distributing tips to, and detaching them from, the distributing units of sample-distributing section 30. This mechanism 90 comprises support plates 91 (only one shown), boxes 92 (only one shown) fastened to plates 91, and plugs 93 (only one shown) suspended from boxes 92. Air pipes 20 are connected to the upper ends of boxes 92. Plugs 93 are made of, for example, hard rubber and shaped such that they can be inserted into the proximal ends of tips 3. They have through holes and are connected by air pipes to boxes 92. The through holes of plugs 93 thus communicate with air pipes 20. A coil spring 94 is interposed between each box 92 and each plug 93, and is mounted on the pipe connecting the plug to the box. O-ring 95 is mounted on the outer periphery of each plug 93, for accomplishing a sufficiently airtight connection between plug 93 and tip 3.

Mechanism 90 further comprises jig 100 fastened to housing 1. Jig 100 is a rectangular plate having five semicircular cut-outs 101 to 105 made in one longer side. Cut-outs 101 to 105 have such a radius that plugs 93 can be inserted into them, but the proximal ends of tips 3 cannot be inserted into them. Jig 100 can be moved relative to the distribution tips, in both the vertical direction and the horizontal direction, by means of a drive mechanism (not shown).

Mechanism 90 operates in the following manner to attach tips 3 to, and detach them from, the distributing units of sample-distributing section 30. To attach tips 3 to distribution units 31 to 35 of section 30, the drive mechanism (not shown) is operated, thus moving sample-distributing section 30 such that plugs 93 are placed above tips 3 held in a rack (not shown). Then, the drive mechanism is operated, lowering section 30 this time, so that plugs 93 are inserted into the proximal ends of tips 3. Since coil springs 94 exert a constant force on plugs 93, plugs 93 are inserted into the proximal ends of tips smoothly and stably. Further, O-rings 95 mounted on plugs 93 are in complete contact with the inner peripheries of tips 3, a sufficiently airtight connection between tips 3 and plugs 39 is accomplished. The drive mechanism (not shown) then moves section 30 upward, thus lifting tips 3, now coupled to units 31 to 35, from the rack. To detach tips from distribution units 31 to 35, the drive mechanism is operated, thus moving section 30 such that tips 3 are moved in the direction of the arrow indicated by the one-dot, one-dash line. As units 31 to 35 are moved upward at semicircular cut-outs 101 to 105 of jig 100, plugs 93, whose diameters are smaller than the radii of the cut-outs, are lifted through the cut-outs, but tips 3, whose proximal ends have diameters greater than the radii of the cut-outs, cannot be lifted. As units 31 to 35 are further moved upward, plugs 93 are pulled out of the proximal ends of tips 3, and tips 3 eventually fall. Therefore, mechanism 90 automatically and smoothly replaces the used tips with new ones.

The present invention is not limited to the embodiment described above. It can also apply to apparatuses for automatically distributing sample liquids other than serum.

What is claimed is:

1. An apparatus for distributing sample liquids contained in a plurality of source test tubes into a plurality of destination test tubes, comprising:
   a plurality of distribution units having a plurality of plugs each provided with an O-ring for air-tight sealing at an outer periphery thereof, and being formed of a cylindrical body including a through-hole at a center portion thereof;
   a plurality of distribution tips fitted to said plugs, said tips being arranged so that a distal end portion of each of said tips can be inserted into and taken out of the corresponding one of said source test tubes, and a proximal opening portion thereof is detachably fitted with the corresponding one of said plugs of said distribution units;
   adjusting means for varying and setting the interval between any two of said plurality of distribution units, which are next to each other, so that the interval between said distribution tips coincides with each of the intervals between said source test tubes and/or said destination test tubes;
   a plurality of air-operated systems provided for said distribution units, and having a function of sucking and holding the sample liquids contained in said source test tubes, and a function of discharging the sample liquids held in said distribution tips into said destination test tubes;
   a mechanism for moving all of said distribution units simultaneously so that said distribution tips, which are holding the sample liquids sucked in by said air-operated systems, are transferred from a first position where said source test tubes are disposed to a second position where said destination test tubes are disposed;
   catching means for catching liquid leaking from said distribution tips while the distribution tips are transported by said moving mechanism, said catching means having a tray driven so that it is always located beneath all of said distribution tips while transporting the tips; and
   automatic replacing means for replacing said distribution tips, in which after the sample liquids held in said distribution tips are discharged by said air-operated systems into said destination test tubes, said distribution tips are removed from said plugs by hitching the proximal opening end of each of said distribution tips on a semicircular-shaped notch formed on a plate member for removing said tips, so as to mount new distribution tips on said plugs;
   each of said plurality of air-operated systems comprising:
   an air pipe having openings at both ends, one of which is connected to the corresponding one of said plugs of said distribution tips;
   a changeover valve having a common air-inlet port connected to the other end of said air pipe, and first and second air-inlet ports, one of which is selected to be connected to said common air-inlet port;

an air-supplying device connected to said first air-inlet port of said changeover valve, for supplying a small amount of air to be discharged from said distal end of the corresponding one of said distribution tips thereto;

a pressure detector for detecting a change of the pressure of the air being supplied from said air-supplying device and generating a signal upon detecting the change of the air pressure;

a changeover means for switching said changeover valve from said first air-inlet port to said second air-inlet port in response to the signal generated from said pressure detector; and an air piston/cylinder device connected to said second air-inlet port of said changeover valve, for sucking and holding the liquid contained in the corresponding one of said source test tubes in the corresponding one of said distribution tips, and for discharging the liquid held in said corresponding one of said distribution tips into the corresponding one of said destination test tubes.

2. An apparatus for distributing sample liquids according to claim 1, wherein the tray for catching the liquid beneath said distribution tips is slidably movable in a horizontal direction by a driving piston/cylinder device.

3. An apparatus for distributing sample liquids according to claim 1, wherein means are provided for adjusting a suction force established by said air piston/cylinder device to retain the liquids contained in said distribution tips.

* * * * *